United States Patent [19]

Moore

[11] Patent Number: 4,514,019
[45] Date of Patent: Apr. 30, 1985

[54] PORTABLE DENTAL OPERATORY

[75] Inventor: Peter E. Moore, Redmond, Wash.

[73] Assignee: Mobile Dental Equipment Corporation, Redmond, Wash.

[21] Appl. No.: 285,155

[22] Filed: Jul. 20, 1981

[51] Int. Cl.³ .............................................. A47B 43/00
[52] U.S. Cl. .................................... 312/209; 312/244; 312/258; 312/DIG. 33
[58] Field of Search ............... 312/209, 208, 204, 223, 312/258, 259, 224, 225, DIG. 33, 244, 274, 275; 108/33, 34; 206/216

[56] References Cited

U.S. PATENT DOCUMENTS

| | | | |
|---|---|---|---|
| 344,132 | 6/1886 | Palmer | 312/224 |
| 941,013 | 11/1909 | Doble et al. | 312/258 |
| 941,608 | 11/1909 | Benson | 312/209 |
| 3,695,746 | 10/1972 | Youngblood | 312/258 |
| 3,848,944 | 11/1974 | Gilmer, Jr. | 312/244 |
| 4,285,556 | 8/1981 | Loeffel | 312/DIG. 33 |
| 4,288,134 | 9/1981 | Knaack et al. | 312/244 |
| 4,294,348 | 10/1981 | Hastings | 312/DIG. 33 |
| 4,294,496 | 10/1981 | Murez | 312/208 |

Primary Examiner—Victor N. Sakran
Attorney, Agent, or Firm—Christensen, O'Connor, Johnson & Kindness

[57] ABSTRACT

A portable, self-contained dental operatory is disclosed. The operatory includes all of the equipment necessary for the ordinary practice of dentistry contained in a cabinet that serves both as a compact carrying case and as a chairside dental workbench. The cabinet includes foldable front and top panels that fold outwardly and downwardly to form a dental workbench positioned in front of a tool support panel that supports dental handpieces and other equipment. The cabinet further contains an electric air compressor that supplies pressurized air to drive the handpieces and to provide a source of pressurized water from a water reservoir. The operatory further includes a vacuum bottle that may be selectively evacuated by the air compressor as required to operate an oral saliva evacuator. The air compressor includes an electric motor that can be tapped to drive grinding and polishing equipment. Such grinding and polishing equipment is located within a removable enclosure that doubles as an X-ray film development chamber and as a dust hood for grinding operations.

24 Claims, 9 Drawing Figures

PORTABLE DENTAL OPERATORY

BACKGROUND OF THE INVENTION

The present invention is related generally to dental equipment and, more particularly, to portable dental equipment.

There exists a need for the delivery of dental services to individuals in remote communities, the disabled, and others who are unable to routinely visit a dental office. Dental care has been largely unavailable to such persons, at least partially because the practice of dentistry requires certain pieces of equipment that are ordinarily in the form of semipermanent fixtures in a dental office. Such equipment includes various dental drills and other handheld tools, X-ray film development and viewing facilities, grinding and polishing equipment, and supporting pneumatic and mechanical power supplies. Although none of this equipment need be large or unwieldy, there has not been previously available a compact, self-contained assembly that includes all of the necessary equipment in a container that is easily portable and which also supports such equipment in a manner conducive to its use in the field.

Accordingly, it is the object and purpose of this invention to provide a compact, portable, self-contained dental operatory.

It is also an object to provide such an operatory having pneumatic pressurization and vacuum functions as well as a mechanical power supply for driving polishing and grinding equipment. It is another object to provide a portable dental operatory having an enclosure for development of X-ray film. It is yet another object to provide a portable dental operatory having a dust hood for grinding and polishing operations. It is another object to provide a portable dental operatory having self-contained vacuum and water reservoirs.

It is also an object of this invention to provide a cabinet for such a portable dental operatory. More specifically, it is an object to provide a cabinet suitable for transporting all of the necessary equipment for routine dentistry and which also serves as a chairside dental work station. In this regard, it is a further object to provide a cabinet that supports a compressor, lighting fixtures, water and vacuum reservoirs, and other equipment necessary for the ordinary practice of dentistry. Additionally, it is an object to provide such a cabinet that further includes an enclosure for an X-ray film development chamber and for grinding and polishing operations.

SUMMARY OF THE INVENTION

In accordance with the present invention, there is provided a portable, self-contained dental operatory that supports all of the equipment necessary for the ordinary practice of dentistry. The operatory includes a cabinet that is particularly adapted to support such equipment in a manner that efficiently combines certain functions so as to minimize the size, weight and complexity of the operatory. The cabinet is constructed to securely hold the various pieces of equipment for transport, and is sufficiently compact to be readily carried by a dentist in the field. The cabinet further serves as a chairside dental work station that supports the various pieces of dental equipment in a presentable and orderly arrangement, and which also contains the necessary supporting equipment, such as a pneumatic pump, a water supply and vacuum apparatus. In particular, the cabinet includes hinged top and side panels that may be unfolded and deployed to form a dental workbench. The cabinet also includes a central, upright tool support panel that supports dental handpieces and other handheld equipment in a readily accessible arrangement. The workbench extends from the base of the tool support panel.

In accordance with other aspects of the invention, the cabinet further includes a removable enclosure that doubles as an X-ray film development chamber and as a dust hood for dental grinding and polishing operations, and which also forms an exterior structural element when the cabinet is assembled for transport.

In another aspect of the invention, the operatory cabinet supports an electric air compressor. The air compressor provides pressurized air to drive a set of dental handpieces and also provides a source of vacuum to an oral evacuator. Additionally, the compressor pressurizes a water reservoir that provides water to a three-way air/water syringe and to an ultrasonic cleaner. Further, the compressor is preferably adapted to drive dental grinding and polishing apparatus that may be located either in the aforementioned cabinet enclosure or coupled to a flexible drive shaft.

These and other aspects and advantages of the invention will be apparent to one of ordinary skill upon reading the following detailed description with reference to the accompanying drawings.

DETAILED DESCRIPTION OF THE PREFERRED EMBODIMENT

Figure 1:
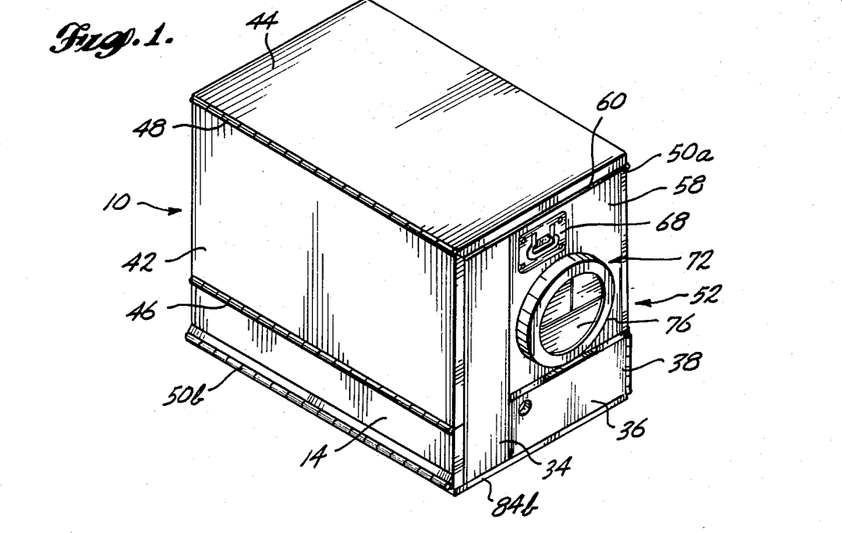
FIG. 1 is an isometric front view of one embodiment of a dental operatory cabinet constructed in accordance with the invention, with the cabinet assembled for transport.
Figure 2:
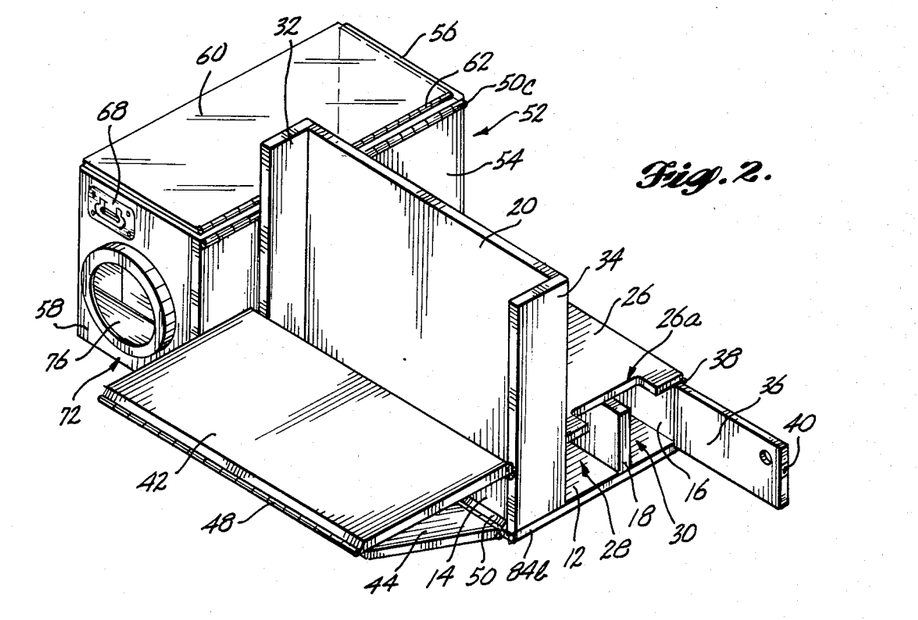
FIG. 2 is an isometric view as in FIG. 1, with the cabinet deployed for use in the field, and with the dental equipment omitted for purposes of illustration.
Figure 3:
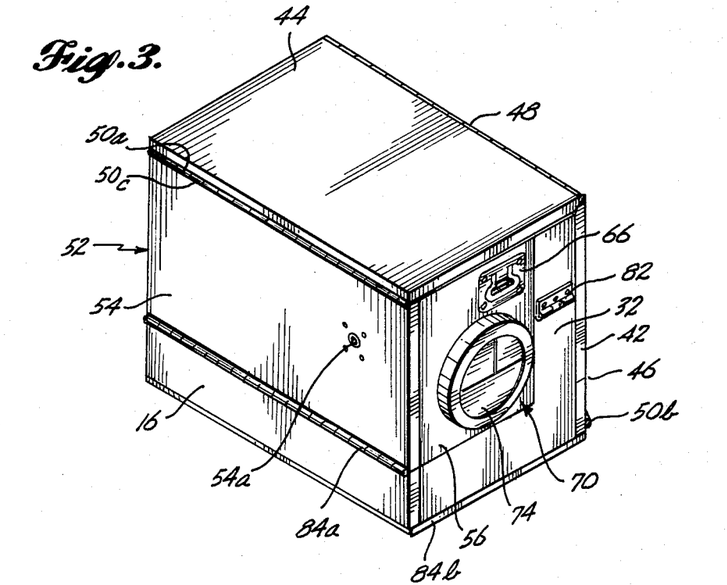
FIG. 3 is an isometric rear view of the assembled cabinet of FIG. 1.

FIGS. 1 through 4B illustrate the preferred embodiment of an operatory cabinet 10 constructed in accordance with the invention, with the various pieces of dental equipment removed for purposes of illustration. When fully assembled for transport, the cabinet 10 is generally rectangular in plan and side views, as shown in FIGS. 1 and 3. The cabinet 10 rests on a rectangular base panel 12. Extending upwardly from the longitudinal edges of the base panel 12 are short, front and rear sidewalls 14 and 16, respectively. An upright supporting wall 18 also extends upwardly from the base panel 12 to the height of the front and rear sidewalls. The supporting wall 18 is located between the sidewalls 14 and 16 and is oriented parallel to the sidewalls 14 and 16. Also affixed to the base panel 12 is a large, upright tool support panel 20 that extends upwardly to the full height of the assembled cabinet. The panel 20 is located between the supporting wall 18 and the front sidewall 14, and is oriented parallel to the sidewalls 14 and 16 and the supporting wall 18. The front and rear sidewalls 14 and 16, the supporting wall 18, and the tool support panel 20 are thus all parallel to one another and extend generally parallel to the longitudinal axis of the rectangular base panel 12.

The cabinet 10 further includes a rectangular, fixed support panel 26 mounted on the upper edges of the rear sidewall 16 and the supporting wall 18. The support panel 26 is oriented substantially horizontally and is parallel to the base panel 12. The inner edge of the support panel 26 abuts the rear side of the tool support panel 20 at a right angle. The underlying supporting wall 18 divides the space between the support panel 26 and the base panel 12 into a pair of elongated storage enclosures 28 and 30. The enclosure 28 is formed between the tool panel 20 and the supporting wall 18; and the enclosure 30 is formed between the supporting wall 18 and the rear sidewall 16. The enclosures 28 and 30 hold water and vacuum bottles, as described further below.

The cabinet 10 further includes a planar, L-shaped end panel 32 (best shown in FIG. 3). The end panel 32 is affixed to one end of the cabinet 10 that is hereinafter referred to as the left-hand end. One arm of the L-shaped panel 32 extends the width of the cabinet 10 and covers the ends of the enclosures 28 and 30. The other arm of the L-shaped panel 32 extends upwardly from the base panel 12 to the top of the tool support panel 20, with the inside edge of the upright arm of the L-shaped panel 32 extending along the end edge of the tool panel 20. The outer edge of the upright arm of the L-shaped panel 32 extends upwardly along the front, left-hand corner of the cabinet 10.

The opposite, or right-hand, end of the cabinet 10 includes a narrow rectangular end panel 34, shown best in FIG. 1. The end panel 34 extends upwardly from the base panel 12 to the top of the tool support panel 20, and is oriented at a right angle with respect to the panel 20. More specifically, one longitudinal edge of the rectangular end panel 34 extends along the edge of the tool panel 20, with the other longitudinal edge of the end panel 34 extending upwardly from the end of the front sidewall 14 to form the front, right-hand corner of the cabinet 10. The end panels 32 and 34 and the tool panel 20 thus form a shallow, channel-shaped structure, as viewed from above.

The cabinet 10 further includes a rectangular door 36 that covers the ends of the enclosures 28 and 30 at the right-hand end of the cabinet 10. One end of the door 36 is connected to the end edge of the rear sidewall 16 by an upright hinge 38 for swinging motion in a horizontal plane. The door 36 is secured in its closed position by means of a spring-loaded ball latch mechanism 40 that is attached to the free end of the door 36 and which is engageable with a cooperable detent (not shown) in the edge of the end panel 34.

The cabinet 10 further includes foldable front and top panels 42 and 44, respectively. The front panel 42 is generally rectangular and is hinged along one longitudinal edge to the upper edge of the front sidwewall 14 by a piano hinge 46. With the cabinet assembled for transport, the front panel 42 extends upwardly in coplanar alignment with the front sidewall 14 to the top of the cabinet 10, as shown in FIGS. 1 and 3.

The top panel 44 is rectangular in configuration and is of the same dimensions as the base panel 12. The top panel 44 includes first and second longitudinal edges. The first edge is hinged to the upper edge of the front panel 42 by a piano hinge 48. With the cabinet 10 assembled for transport, the top panel 44 extends horizontally across the top of the cabinet 10, with the piano hinge 48 extending along the upper front corner of the cabinet 10.

The top panel 44 and the front panel 42 are foldable outwardly and downwardly from the cabinet 10 to form a horizontal working surface, as shown best in FIG. 2. In this position, the front panel 42 extends horizontally outwardly from the top edge of the front sidewall 14, such that the inside surface of the front panel 42 forms a horizontal working surface. The top panel 44 is folded about the piano hinge 48 all the way around the outer edge of the front panel 42 and is connected along its second longitudinal edge to the bottom edge of the front sidewall 14 by a piano hinge assembly 50 so as to brace the front panel 42 in the horizontal position. In this regard, the second edge of the top panel 44 and the lower edge of the front sidewall 14 are provided with cooperable half-hinges 50a and 50b, respectively which intermesh to form the piano hinge assembly 50. The two half-hinges 50a and 50b are intermeshed and engaged with a removable hinge pin to secure the second edge of the top panel 44 to the bottom of the front sidewall 14.

The cabinet 10 further includes a removable, multi-purpose enclosure 52. The removable enclosure 52 includes three fixed walls; an upright rectangular rear wall 54 and a pair of opposing end walls 56 and 58. The enclosure 52 further includes a substantially transparent, amber-tinted plastic top panel 60 that is hinged to the upper edge of the rear wall 54 by a piano hinge 62. The plastic panel 60 ordinarily rests in a horizontal orientation on the upper edges of the rear wall 54 and the end walls 56 and 58. The enclosure further includes a half-hinge 50c along the upper edge of the rear wall 54.

Figure 4A:
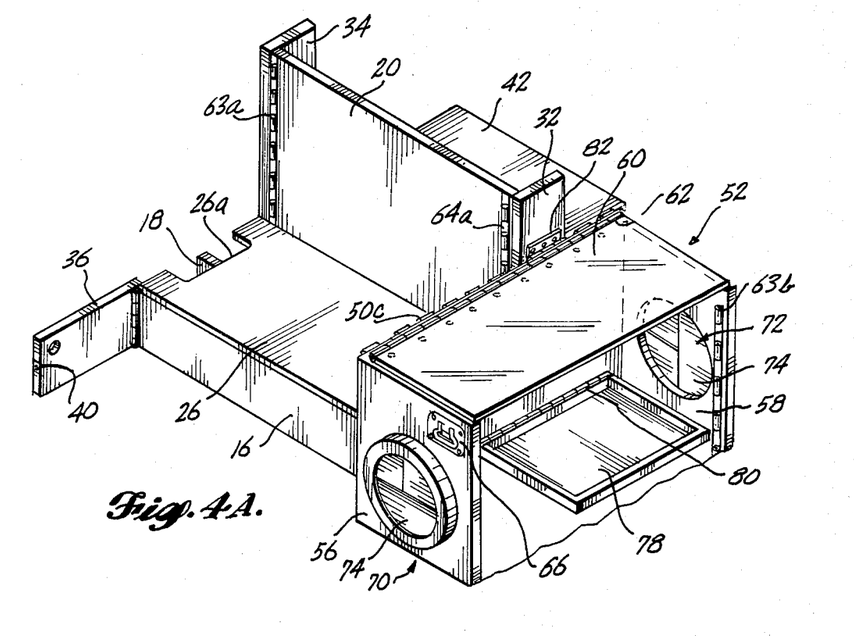
FIG. 4A is an isometric rear view as in FIG. 3, with the cabinet deployed as in FIG. 2.

With the cabinet 10 assembled for transport, the removable enclosure 52 rests on the support panel 26, as shown best in FIG. 3. In this position, the rear wall 54 of the removable enclosure 52 extends upwardly in alignment with the rear sidewall 16, and the end walls 56 and 58 of the removable enclosure 52 are coplanar with the end panels 32 and 34, respectively. Further, the plastic top panel 50 of the removable enclosure 52 lies immediately beneath the foldable top panel 44. The removable enclosure 52 is secured in this position on the support panel 26 by a pair of two-piece piano hinge assemblies that comprise a pair of half-hinges 63a and 64a affixed to the back side of the tool support panel 20, and a pair of half-hinges 63b and 64b affixed to the edges of the enclosure end walls 56 and 58, respectively (FIG. 4A). The piano hinge assemblies 63a–63b and 64a–64b connect the front edges of the enclosure end walls 56 and 58 to the back side of the upright tool support panel 20. To prepare the cabinet for transport, the removable enclosure 52 is positioned on the support panel 26 and the half-hinges 63a and 64b are intermeshed with the half-hinges 63b and 64b. Removable piano hinge pins (not shown) are then inserted in the completed hinge assemblies to secure the enclosure 52 to the tool support panel 20. Additionally, the top panel 44 is secured to the upper edge of the rear wall 54 of the enclosure 52 by means of the half-hinge 50c mounted on the rear wall 54 and the cooperable half-hinge 50a affixed to the edge of the top panel 44. A removable hinge pin (not shown) is inserted in the intermeshed half-hinges 50a and 50c to secure the top panel 44 to the enclosure 52.

The removable enclosure 52 further includes carrying handles 66 and 68 affixed to the end walls 56 and 58, respectively. Further, the removable enclosure 52 includes circular access openings 70 and 72 in the end walls 56 and 58, respectively. The access openings are covered with opaque, elastic nylon seals 74 and 76, respectively, for reasons set forth more fully below. Additionally, the removable enclosure 52 includes a foldable pumice tray 78 that is pivotably connected to the lower edge of the inside surface of the rear enclosure wall 54 by a piano hinge 80.

The cabinet 10 is deployed for use by arranging the top and front panels 44 and 42 to form the work surface shown in FIG. 2, and by removing the enclosure 52 and securing it to the left-hand end of the cabinet 10, as shown in FIGS. 2 and 4A. In this regard, the back side of the enclosure rear wall 54 is set against the L-shaped end panel 32 such that the enclosure 52 opens outwardly away from the left-hand end of the cabinet 10. In this position, the half-hinge 50c along the upper edge of the rear enclosure wall 54 meshes with a short half-hinge 82 affixed to the L-shaped end panel 32. A removable hinge pin (not shown) is inserted in the intermeshed half-hinges 50c and 82 to secure the enclosure 52 to the end panel 32 as shown in FIG. 4A. The enclosure 52 then serves a dual purpose; as an X-ray film development chamber and as a dust hood for grinding and polishing operations. In use of the enclosure as an X-ray development chamber, the front panel 42 may be removed from its ordinary position and attached to the front of the enclosure 52 to prevent light from entering the enclosure 52 during development of X-ray film. The amber tint of the plastic top panel 60 of the enclosure 52 permits development of dental X-ray film, which is not particularly light-sensitive and can be developed in the removable enclosure 52 under such conditions. The elastic nylon rubber seals 74 and 76 permit the operator to manually conduct the necessary film development operations inside the enclosure with a minimum amount of light entering the enclosure through the openings 70 and 72.

Figure 4B:
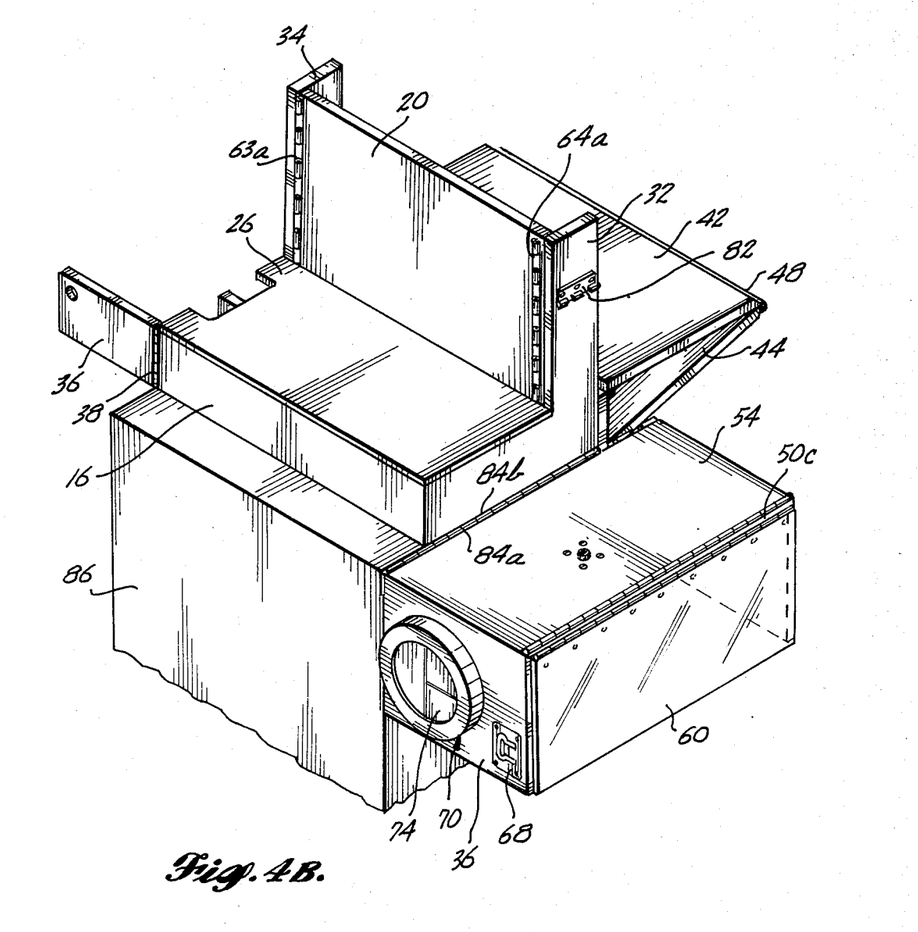
FIG. 4B is an isometric view as in FIG. 4A, with the cabinet deployed in an alternative configuration.

In an alternative configuration shown in FIG. 4B, the enclosure 52 may be swung downwardly from the position shown in FIG. 4A, such that the rear wall 54 of the enclosure forms a second horizontal work surface, as shown in FIG. 4B. In this regard, a half-hinge 84a is affixed to the lower edge of the rear enclosure wall 54; and a cooperable half-hinge 84b is affixed to the lower edge of the L-shaped end panel 32. The half-hinges 84a and 84b are intermeshed and secured with a removable hinge pin (not shown) to support the enclosure in the position shown in FIG. 4B. Ordinarily, the cabinet 10 will be set on a supporting table or other structure (indicated as 86 in FIG. 4B) to stabilize the enclosure 52 in the alternative position.

Figure 5:
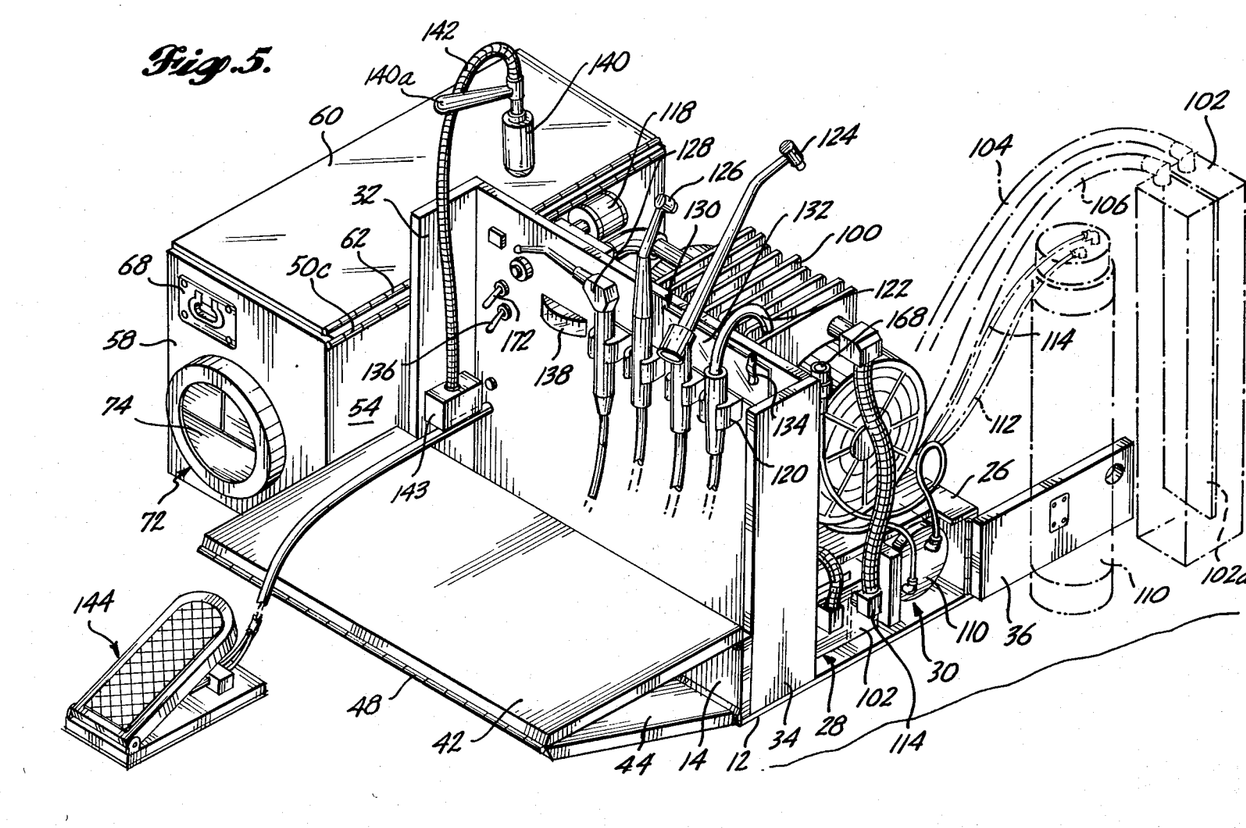
FIG. 5 is an isometric front view of the complete operatory, including the various pieces of dental equipment as they are arranged for use in the field.
Figure 6:
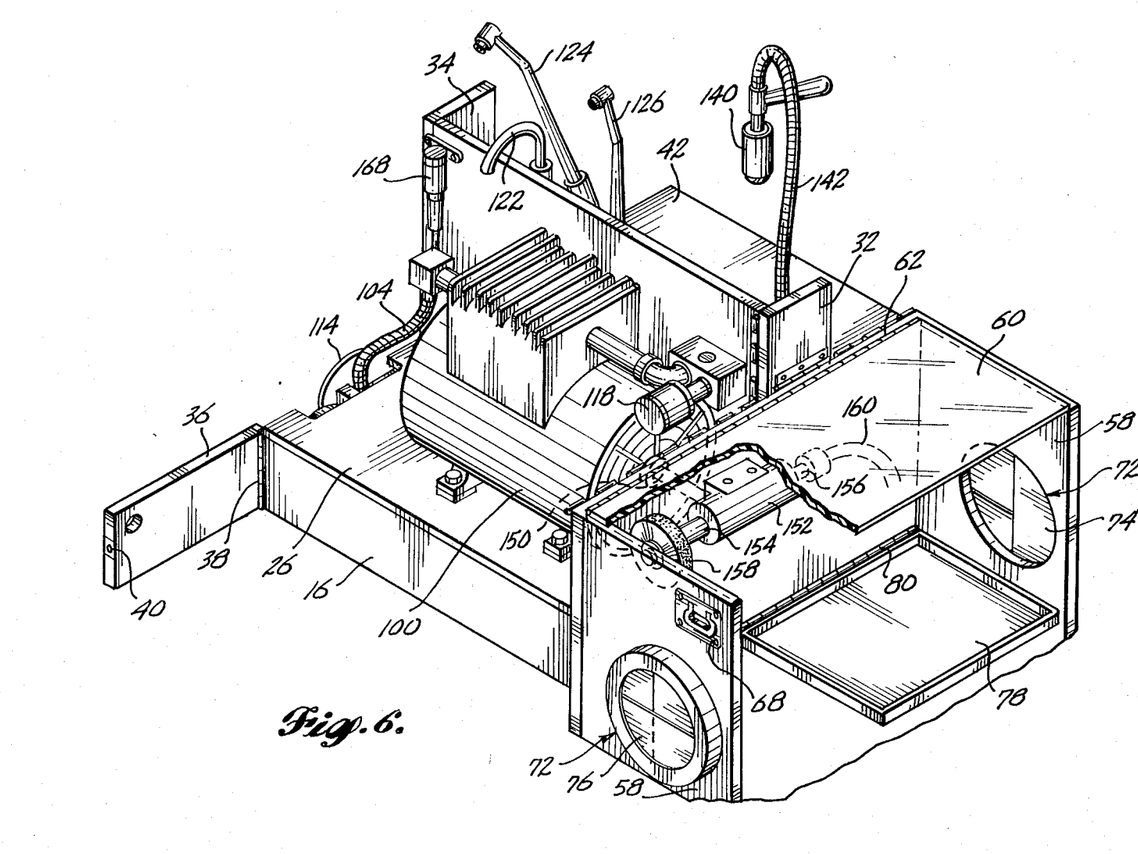
FIG. 6 is an isometric rear view of the operatory as in FIG. 6, showing the compressor and a removable enclosure.

Turning now to FIGS. 5 and 6, the cabinet 10 supports all of the equipment necessary for the ordinary practice of dentistry. A 110-volt AC electric air compressor 100 is mounted on the support panel 26. The electric compressor 100 provides both pneumatic and mechanical power to various pieces of equipment. More specifically, the compressor 100 provides pressurized air to drive dental handpieces (drills) and to pump water. Also, the compressor 100 provides a source of vacuum. Additionally, the armature of the internal electric motor of the compressor 100 is tapped in a manner further described below to provide mechanical power to a grinding and polishing apparatus, and to a dental amalgamator.

The air intake of the electric compressor 100 is coupled to a transparent vacuum bottle 102 via a vacuum line 104. The vacuum bottle 102 is normally stored in the elongate enclosure 28 beneath the support panel 26. The support panel 26 includes a cutout 26a that permits the vacuum bottle 102 to be coupled to the compressor 100 via the line 104 when the vacuum bottle 102 is stored in the enclosure 28 and the door 36 is closed.

A second vacuum line 106 is also connected to the top of the vacuum bottle 102. The vacuum line 106 passes through a hole in the upright tool support panel 20 and may be connected to an oral saliva evacuator or other dental equipment. The vacuum bottle 102 is transparent so that it may be routinely inspected after each use. Further, the bottle contains an internal baffle 102a.

The air output of the air compressor 100 is connected to a water bottle 110 that is ordinarily stored in the enclosure 30 beneath the support panel 26. A high-pressure air line 112 connects the output of the air compressor 100 to the water bottle 110 via a pressure manifold described below. A water output line 114 conducts water from the water bottle 110 to an oral irrigator and to a water-cooled handpiece, as also described further below. The compressor 100 can be exhausted after use by means of a compression release valve (described further below) and an exhaust muffler 118.

A tool rack 120 affixed to the front side of the tool support panel 20 supports various hand-held dental tools, including an oral saliva evacuator 122, a high-volume oral evacuator (not shown), a low-speed dental handpiece 124, a high-speed water-cooled handpiece 126, and a three-way air/water/spray syringe 128. Details regarding the structure and use of these pieces of equipment will be apparent to one of ordinary skill in the art.

The tool support panel 20 further supports an X-ray film viewer 130. The film viewer 130 includes a light source (not shown) emplaced behind a translucent window 132 set into the front surface of the tool support panel 20. Film clips 134 are provided to hold X-ray film in place over the translucent window 132. The light source is actuated by a switch 136 on the tool support panel 20. The tool support panel 20 further supports a pressure gauge 138 that monitors the air pressure in the compressor 100.

A high-intensity incandescent lamp 140 is mounted on a flexible shaft 142 that extends from a transformer base 143. The base 143 is mounted on the inside surface of the cabinet end panel 32. The lamp 140 includes a handle 140a by which the lamp 140 may be selectively positioned to illuminate a patient's mouth, the working surface formed by the foldable front panel 42, or the interior of the enclosure 52.

The operatory further includes a footpedal valve 144 that controls the speed of the high- and low-speed handpieces 126 and 124, as further described below.

Referring particularly to FIG. 6, the armature shaft of the electric motor in the compressor 100 may be tapped with a removable extension shaft 150. With the removable enclosure 52 set against the left-hand end of the cabinet 10, the extension shaft 150 passes through a hole 54a (shown in FIG. 3) in the rear wall 54 of the enclosure 52. The shaft 150 is engaged with a gearbox assembly 152 affixed to the rear wall 54 of the enclosure 52. The gearbox assembly 152 includes two oppositely extending output shafts 154 and 156. A grinding wheel 158 is attached to the end of the output shaft 154. The other output shaft 156 may be coupled to a flexible drive shaft 160, as shown in FIG. 6, or may be provided with a buffing wheel or other device. The flexible shaft 160 is ordinarily coupled to a hand-held buffing or grinding wheel.

Alternatively, the armature shaft 150 of the compressor 100 may be coupled directly to an amalgamator, (not shown) the structure and function of which will be apparent to one of ordinary skill in the art.

Figures 7, 8:
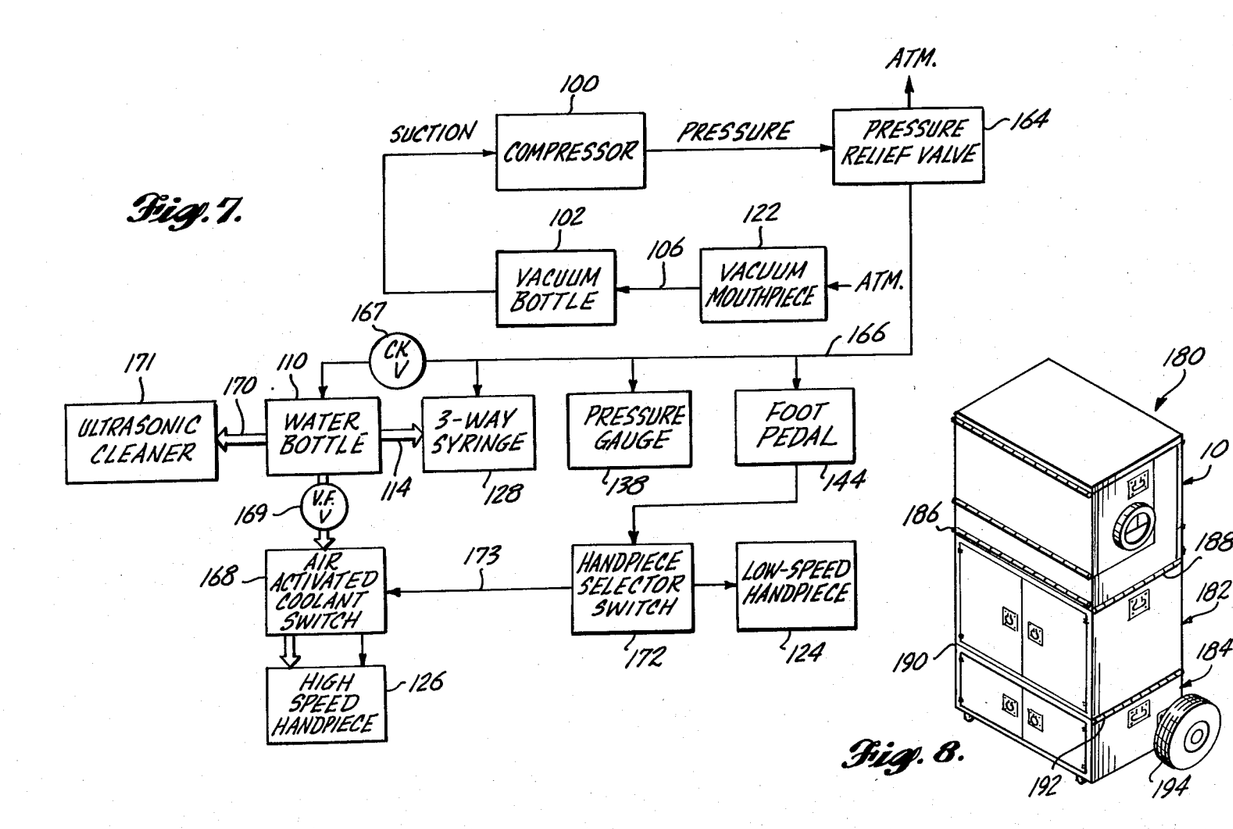
FIG. 7 is a functional block diagram of the operatory.
FIG. 8 is an isometric view of the operatory assembled for transport and in combination with a storage cabinet and a portable X-ray generator forming a three-part wheeled assembly.

FIG. 7 illustrates schematically the operation of the pneumatic functions of the operatory. Air is drawn into the electric compressor 100 through the vacuum bottle 102 and the various oral evacuation devices. The compressor 100 supplies pressurized air to a pressure-relief valve 164. The compressor also supplies pressurized air to a manifold line 166. Pressurized air is distributed from the manifold line 166 to the footpedal valve 144, the pressure gauge 138, the three-way syringe 128, and the water bottle 110. A check valve 167 is interposed between the manifold 166 and the water bottle 110.

The water bottle 110 supplies pressurized water, indicated by heavy arrows in FIG. 7, to the three-way syringe 128 and to an air-activated coolant switch 168. A variable flow valve 169 is interposed between the water bottle 10 and the coolant switch 168 to control the flow of water to the switch 168. Also, an auxiliary water output 170 is provided from the water bottle 110 for use with an ultrasonic cleaner 171.

The footpedal valve 144 meters pressurized air from the manifold line 166 to a handpiece selector switch 172 that is located on the front side of the tool support panel 20. The handpiece selector switch 170 diverts pressurized air to either the low-speed handpiece 124 or to the high-speed water-cooled handpiece 126 via a pressure line 173 and the air-activated coolant switch 168. The coolant switch 168 is actuated by the pressurized air in line 173 to admit pressurized water to the high-speed handpiece 126, such that the high-speed handpiece 126 is supplied with both coolant water and pressurized air upon actuation of the selector switch 172 and the footpedal 144.

It will be seen that the cabinet 10 provides a combination of functions that minimizes the size and weight of the operatory, yet permits it to include all of the necessary tools for the ordinary practice of dentistry. For example, the foldable top and front panels 44 and 42 form sturdy exterior cabinet panels during transport of the operatory, and also cooperate during use of the operatory to form a conveniently arranged chairside dental work space wherein the various dental handpieces are conveniently arranged for ready access above the workbench formed by the front panel 42. Further, when the cabinet is assembled for transport the front panel 42 and the tool support panel form a narrow, deep enclosure that is particularly well suited for holding the coiled lengths of pneumatic tubing connected to the handpieces mounted on the tool panel 20.

Also, the removable enclosure 52 is sized to cooperably enclose the compressor 100 and form an integral part of the assembled cabinet during transport, yet also serves as both an X-ray film development chamber and a dust hood for grinding and polishing operations.

The operatory cabinet 10 forms one element of a three-cabinet assembly 180 mounted on wheels, as shown in FIG. 9. The assembly 180 shown in FIG. 9 includes the operatory cabinet 10, a storage cabinet 182, and a portable X-ray generator 184. The operatory 10 rests on the storage cabinet 182 and is secured in place by means of piano hinge assemblies 186 and 188. The storage cabinet 182 in turn rests on the X-ray generator 184 and is secured thereto by piano hinge assemblies 190 and 192. The X-ray generator 184 is mounted on a wheel assembly 194. The cabinet 182 and the X-ray generator 184 augment the operatory 10 to form a complete, portable dental laboratory.

Although the present invention is described and illustrated by reference to a preferred embodiment, it will be understood that various alterations, modifications and substitutions that may be apparent to one of ordinary skill in the art may be made without departing from the spirit of the invention. Accordingly, the scope of the invention is defined by the following claims.

The embodiments of the invention in which an exclusive property or privilege is claimed are defined as follows:

1. A portable dental operatory comprising:
   a cabinet, said cabinet including a generally rectangular base having front and rear sides, an upright tool support panel mounted on said base between said front and rear sides and extending substantially parallel to said front and rear sides, a front panel having first and second opposite edges, said front panel being hinged along said first edge to said front side of said base for swinging motion between an upright position wherein said front panel is substantially parallel to said tool support panel and a substantially horizontal position wherein said front panel extends from said base to form a work surface positioned in front of said tool supprt panel, a top panel having first and second edges, said first edge of said top panel being hinged to said second edge of said front panel for relative folding motion of said top panel and said front panel, connecting means for attaching said second edge of said top panel to said base beneath said first edge of said front panel such that said top panel braces said front panel in said substantially horizontal position, and whereby said top panel is foldable upwardly and over said tool support panel to assemble said cabinet for transport;
   an electric air compressor mounted on said base behind said tool support panel; and
   a removable enclosure mountable on said base behind said tool support panel so as to enclose said air compressor, said removable enclosure including a rear wall and opposing end walls, said removable enclosure further including a substantially transparent top panel hinged to the upper edge of said rear wall, means for attaching said enclosure to said cabinet, and connecting means for attaching said second edge of said top panel to said removable enclosure so as to assemble the operatory for transport.

2. The portable dental operatory defined in claim 1 wherein said removable enclosure includes manual access openings in said end walls and rubber seals for restricting entry of light through said openings.

3. The portable dental operatory defined in claim 1 wherein said base of said cabinet includes a generally rectangular base panel having front and rear edges, front and rear sidewalls extending upwardly from said front and rear edges of said base panel, respectively, a supporting panel extending upwardly from said base panel between said rear sidewall and said tool support panel and oriented substantially parallel to said rear sidewall, a support panel mounted on said rear sidewall and said supporting wall, said air compressor being mounted on said support panel, said support panel and said base panel thereby forming a pair of elongate enclosures.

4. The portable dental operatory defined in claim 3 further comprising water and vacuum bottles adapted to be contained in said enclosures in said base, the air output of said air compressor being connected to said water bottle to provide a source of pressurized water, and the air intake of said air compressor being selectively connectable to said vacuum bottle to provide a vacuum reservoir.

5. The portable dental operatory defined in claim 4 further comprising a gearbox mounted on the inside surface of said rear wall of said removable enclosure, said rear wall of said removable enclosure including a drive shaft opening for receiving a drive shaft engaged with said gearbox, said gearbox and said aperture being positioned such that said removable enclosure is positionable against one end of said cabinet to receive a drive shaft of said electric compressor engaged with said gearbox, said gearbox including at least one substantially horizontal output shaft inside said removable enclosure.

6. The portable dental operatory defined in claim 5 wherein said gearbox includes oppositely extending, substantially parallel output shafts, one of said output shafts having grinding wheel means attached thereto, the other of said output shafts being adapted to drive a flexible drive shaft.

7. The portable dental operatory defined in claim 5 further comprising a high-speed handpiece and a low-speed handpiece pneumatically driven by said air compressor, said high-speed handpiece being water-cooled by pressurized water supplied to said high-speed handpiece from said water bottle.

8. The portable dental operatory defined in claim 7 wherein said tool support panel further includes an X-ray film viewer including a translucent window set into said tool support panel and light means emplaced behind said translucent window.

9. A cabinet for a portable dental operatory, comprising a base having front and rear sides, an upright tool support panel mounted on said base between said front and rear sides and extending upwardly from said base, a front panel having first and second edges, said front panel being hinged along said first edge to said front side of said base for swinging motion between an upright position wherein said front panel is substantially parallel to said tool support panel and a substantially horizontal position wherein said front panel extends outwardly from said base to form a work surface in front of said tool support panel, a top panel having first and second edges, said first edge of said top panel being hinged to said second edge of said front panel for relative folding motion, and means for attaching said second edge of said top panel to said base beneath said first edge of said front panel that said top panel braces said front panel in said substantially horizontal position, and whereby said top panel is foldable upwardly and over said tool support panel to assemble said cabinet for transport.

10. The cabinet defined in claim 9 further comprising a removable enclosure mountable on said base behind said tool support panel, said removable enclosure having an upright rear wall and opposing end walls, connecting means for attaching said removable enclosure to said cabinet such that said removable enclosure forms an integral part of said cabinet when assembled for transport, and connecting means for connecting said second edge of said top panel to said removable enclosure to secure said top and front panels for transport.

11. The cabinet defined in claim 10 wherein said removable enclosure includes a substantially transparent top panel hinged to the upper edge of said rear wall of said removable enclosure.

12. The cabinet defined in claim 11 wherein said removable enclosure further includes a pumice tray hinged to the inside surface of said rear wall of said enclosure for swinging motion between a substantially horizontal position and an upright position wherein said pumice tray is folded against said rear wall of said removable enclosure.

13. The cabinet defined in claim 11 wherein said removable enclosure includes a gearbox assembly affixed to the inside of said rear wall, and an aperture in said rear wall for receiving a drive shaft in engagement with said gearbox, said gearbox having at least one output drive shaft extending substantially horizontally therefrom.

14. The cabinet defined in claim 11 wherein said removable enclosure further includes access openings in said end walls of said removable enclosure, said access openings including opaque rubber seals for minimizing entry of light during development of X-ray film in said enclosure.

15. The cabinet defined in claim 10 wherein said base comprises a lower base panel and a support panel spaced upwardly therefrom and oriented substantially parallel thereto, said support panel being spaced from said base panel by front and rear sidewalls extending upwardly from opposite edges of said base panel, said front panel being hinged to the upper edge of said front sidewall of said base, said top panel being attachable along said second edge of said top panel to the lower edge of said front sidewall, and support panel means between said base panel and said support panel for dividing the space between said support panel and base panel into a pair of elongate enclosures for receiving and holding water and vacuum bottles, respectively.

16. The cabinet defined in claim 14 wherein said upright tool support panel includes mounting means attached to the front side thereof for supporting a plurality of dental handpieces.

17. The cabinet defined in claim 14 further including an X-ray viewer including a translucent window set into said tool support panel and light means emplaced behind said translucent window.

18. A cabinet for a portable dental operatory comprising a base having front and rear sides, an upright tool support panel mounted on said base forwardly from said rear side and extending upwardly from said base, said tool support panel having a front side and a rear side, a removable enclosure mountable on said base behind said tool support panel, said removable enclosure having an upright rear wall and opposing end walls, connecting means for attaching said removable enclosure to said cabinet such that the removable enclosure forms an integral part of said cabinet when assembled for transport, an air compressor mounted on said base behind said tool support panel, a gear box mounted on the inside surface of said rear wall of said removable enclosure, said rear wall of said removable enclosure including a drive shaft opening for receiving a drive shaft engaged with said gear box, said gear box and said aperture being positioned such that said removable enclosure is positionable against one end of said cabinet to receive a drive shaft coupled to said compressor, said gear box including at least one substantially horizontal output shaft inside said removable enclosure.

19. The cabinet defined inn claim 18 wherein said front panel includes first and second edges and said top panel includes first and second edges, said front panel being hinged to said front side of said base along said first edge of said front panel, said second edge of said front panel being hinged to said first edge of said top panel, and a means for attaching said second edge of said top panel to said base beneath said first edge of said front panel such that said top panel braces said front panel in a substantially horizontal position to form a work space in front of said tool support panel.

20. The cabinet defined in claim 19 wherein said removable enclosure includes a substantially transparent top panel hinged to the upper edge of said rear wall of said removable enclosure.

21. The cabinet defined in claim 19 wherein said removable enclosure further includes a pumice tray hinged to the inside surface of said rear wall of said enclosure for swinging motion between a substantially horizontal position and an upright position wherein said pumice tray is forward against said rear wall of said removable enclosure.

22. The cabinet defined in claim 19 wherein said cabinet further comprises an end wall extending upwardly from one end of said base, and a means for selectively connecting said rear wall of said removable enclosure to said end wall of said cabinet.

23. The cabinet defined in claim 19 wherein said removable enclosure further includes access openings in said end walls of said removable enclosure, said access openings including opaque rubber seals for minimizing entry of light during development of X-ray film in said enclosure.

24. The cabinet defined in claim 22 wherein said removable enclosure includes a gearbox assembly affixed to the inside of said rear wall, and an aperture in said rear wall for receiving a drive shaft in engagement with said gearbox.

* * * * *